United States Patent
Feldmann et al.

(10) Patent No.: US 10,987,111 B2
(45) Date of Patent: Apr. 27, 2021

(54) SURGICAL DRILL BIT

(71) Applicant: Universitat Bern, Bern (CH)

(72) Inventors: Arne Niklas Feldmann, Bern (CH); Stefan Weber, Boll (CH); Philippe Kurt Zysset, Villars-sur-Glane (CH)

(73) Assignee: Universitat Bern, Bern (CH)

( * ) Notice: Subject to any disclaimer, the term of this patent is extended or adjusted under 35 U.S.C. 154(b) by 58 days.

(21) Appl. No.: 16/072,851

(22) PCT Filed: Jan. 27, 2017

(86) PCT No.: PCT/EP2017/051714
§ 371 (c)(1),
(2) Date: Jul. 25, 2018

(87) PCT Pub. No.: WO2017/129718
PCT Pub. Date: Aug. 3, 2017

(65) Prior Publication Data
US 2019/0029696 A1    Jan. 31, 2019

(30) Foreign Application Priority Data
Jan. 27, 2016  (EP) ...................................... 16153033

(51) Int. Cl.
*A61B 17/16* (2006.01)
(52) U.S. Cl.
CPC .... *A61B 17/1615* (2013.01); *B23B 2251/424* (2013.01)
(58) Field of Classification Search
CPC . A61B 17/1615; A61B 17/16; A61B 17/1617; A61B 17/162; A61B 17/1622;
(Continued)

(56) References Cited

U.S. PATENT DOCUMENTS 5,584,617 A * 12/1996 Houser ................... B23B 51/02
408/1 R
6,641,395 B2 * 11/2003 Kumar ............... A61B 17/1615
433/165
(Continued)

FOREIGN PATENT DOCUMENTS

CH          658 812 A5    12/1986
EP        1 949 858 A1     7/2008
(Continued)

OTHER PUBLICATIONS

International Search Report for Application No. PCT/EP2017/051714 dated Apr. 10, 2017 in 2 pages [the ISR for the PCT Application of this US national phase application].

*Primary Examiner* — Larry E Waggle, Jr.
(74) *Attorney, Agent, or Firm* — Knobbe, Martens, Olson & Bear, LLP

(57) ABSTRACT

A drill bit (1) for creating a tubular hole in a bone (9), comprises: a longitudinal body (2) extending along an axis (21) and having a proximal end and a distal end (22); a main cutting edge (3) formed at the distal end (22) of the body (2); a main cutting face (4) extending from the main cutting edge (3) and defining a rake angle (α); and a spiral flute (5) formed around the body (2) and extending from the main cutting face (4) along the axis (21) of the body (2). The main cutting edge (3) is the only single main cutting edge (3) of the drill bit (1). The spiral flute (5) is the only single spiral flute (5) of the drill bit. The rake angle (α) is at least 25°. The drill bit (1) according to the invention drill bit allows for minimizing heat production when drilling a hole into the bone.

13 Claims, 3 Drawing Sheets

(58) Field of Classification Search
CPC ............ A61B 17/1624; A61B 17/1626; A61B 17/1628; A61B 17/1631; B23B 51/04; B23B 51/02; B23B 2251/04; B23B 2251/14; B23B 2251/18; B23B 2251/408; B23B 2251/424
See application file for complete search history.

(56) References Cited

U.S. PATENT DOCUMENTS

| | | | |
|---|---|---|---|
| 2009/0031871 A1* | 2/2009 | Malandain | A61B 17/32002 83/53 |
| 2011/0238070 A1* | 9/2011 | Santangelo | A61B 17/1635 606/80 |
| 2012/0004661 A1* | 1/2012 | Leppelmeier | A61B 17/1615 606/80 |
| 2013/0274750 A1* | 10/2013 | Schoutens | A61B 17/1615 606/80 |

FOREIGN PATENT DOCUMENTS

| | | |
|---|---|---|
| SU | 1253630 | 8/1986 |
| WO | WO 2004/014241 A1 | 2/2004 |
| WO | WO 2017/129718 A1 | 8/2017 |

\* cited by examiner

SURGICAL DRILL BIT

CROSS-REFERENCE TO RELATED APPLICATIONS

This application is a national stage application under 35 U.S.C. § 371 of International Application No. PCT/EP2017/051714, filed on Jan. 27, 2017, which published in English as WO 2017/129718 A1 on Aug. 3, 2017, and which claims priority benefit of EP Patent Application No. 16153033.2, filed on Jan. 27, 2016.

TECHNICAL FIELD

The present invention relates to a surgical drill bit according to the preamble of independent claim 1. Such drill bits comprising a longitudinal body extending along an axis and having a proximal end and a distal end, a main cutting edge formed at the distal end of the body, a main cutting face extending from the main cutting edge and defining a rake angle, and a spiral flute formed around the body and extending from the main cutting face along the axis of the body, can be used for creating a tubular hole into a bone.

BACKGROUND ART

In many surgical treatments or therapies it is desired to provide one or plural tubular holes into a bone of a patient. For example, dental implants or cochlear implants are typically set into holes provided in jaw or other bones where they firmly connect to the bone. Or, in orthopedic applications often support structures such as metal plates or replacements such as artificial joints or the like are screwed to the associated bones wherein the screws are provided in pre-drilled holes in the bone. Or, in other application it is desired to drill holes in the mastoid of the temporal bones.

For providing holes to bones surgical drills are commonly used. Such drills usually comprise a main apparatus with a drive and a hand piece. Usually the hand piece has a connector to which a drill bit can be rotatably mounted. Such drill bits often comprise a longitudinal body with a sharp distal end and a proximal end formed as a shaft. For mounting, the shaft can be clamped into the connector of the hand piece. At the distal end of the body plural cutting faces are typically shaped which pass over into spiral flutes extending around the body along its axis. A surgical drill bit of the art is, for example, described WO 2013/154686 A1.

In use, for providing a hole into a bone a suitable drill bit is chosen and mounted to the hand piece of the drill. For choosing an appropriate drill bit the size and geometry of the drill bit as well as the conditions of the bone tissue and of the prospective hole are typically considered. The drill bit is then rotated around its axis by the drive of the main piece of the drill wherein depending on the kind of hole, the bone conditions and the type of drill bit an appropriate rotational speed is adjusted. The drill bit is applied to the bone by forwarding it along its axis with its point or tip ahead. Thereby, the cutting face cuts the bone and the chips generated by said cutting are forwarded by the spiral flutes off the bone.

A problem of conventional drills using known drill bits is that heat produced by the drilling can impair the bone tissue around the hole. In particular, such heat can induce carbonization of the bone tissue which might lower the quality of the bone tissue. For example, when the bone tissue is to be connected or grown to any other part, e.g. an implant or a screw, such carbonization hinders a quick healing of the bone and, thus, a quick connection of the bone to the other part.

Therefore, there is a need for a drill or drill bit allowing for minimizing heat production when drilling a hole into a bone.

DISCLOSURE OF THE INVENTION

According to the invention this need is settled by a drill bit as it is defined by the features of independent claim 1. Preferred embodiments are subject of the dependent claims.

In particular, the invention deals with a drill bit for creating a tubular hole in a bone. The drill bit comprises a longitudinal body extending along an axis and having a proximal end and a distal end. It further has a main cutting edge formed at the distal end of the body as well as a main cutting face extending from the main cutting edge. The main cutting face defines a rake angle. The drill bit comprises a spiral flute formed around the body and extending from the main cutting face along the axis of the body. The main cutting edge is the only single main cutting edge of the drill bit. The spiral flute is the only single spiral flute of the drill bit. The rake angle is at least 25°.

The term "drill bit" as used herein can relate to a longitudinal rotatable piece adapted to be mounted to and rotated by a drilling device. Typically, drill bits have an essentially rod like or cylindrical form wherein the circumference is profiled in a particular manner. Often, they are made of a comparably hard material such as a metal, e.g. stainless steel, tungsten carbide or platinum, or a ceramic. The drill bit might be coated to aid chip evacuation or for other purposes. Such coating can, e.g., be diamond-like carbon (DLC), titanium nitride (TIN) or other materials and or layers.

The term "tubular hole" in context of the invention can relate to a linear or non-linear duct or blind hole having a circular or similar cross section.

The term "main" with regard to the cutting edge and the cutting face can relate to a major cutting or major milling portion of the drill bit compared to a cutting or milling by other portions of the drill bit. Typically, the main cutting edge is directed towards the distal end of the body and the main cutting face cuts the bone essentially into the direction of the distal end, i.e., in an axial direction. Often drill bits also have a side cutting edge and a side cutting face which cut the bone in an essentially radial direction.

The term "rake angle" in the context of the invention can relate to an angle of the main cutting face relative to the work. In particular, it can relate to an angle which, in an intended operation of the drill bit, extends between a region of the workpiece where the drill bit acts on and the main cutting face of the drill bit. Thereby, the plane of the workpiece can be the surface to be generated by the drill bit, i.e. an intended new surface. In other words, the rake angle can be between a plane perpendicular to a direction of milling or a direction into which the main cutting face cuts the bone and the main cutting face itself. Furthermore, the rake angle might vary along the main cutting face such as it might decrease towards the center of the drill bit. In such embodiments the term "rake angle" as used in connection with the invention relates to the rake angle at the outer boundary of the drill bit, i.e. at the peripheral or radial end of the main cutting face.

Preferably, the rake angle is defined between the intended new surface of the bone to be generated by the drill bit and the main cutting face of the drill bit less 90°. The term "intended new surface" in connection with drilling the hole into the bone can relate to a surface which is produced by rotating and forcing the drill bit into the bone such that the new surface of the bone is generated. Typically, the new surface lies or is generated in front of the cutting edge and the cutting face in terms of a direction of movement of the drill bit.

Thereby, the intended new surface of the bone preferably is an inner surface of the tubular hole. The term "inner surface" with respect to the tubular hole can relate to the cylindrical peripheral surface of the hole as well as the bottom surface of the hole.

In accordance with the invention, the single cutting edge allows for minimizing an area around the point or tip in which the bone is chiseled rather than being cut. Since chiseling the bone can involve a comparably high heat production compared to cutting the bone, minimizing chiseling within a drilling process allows for reducing heat production.

Thus, by combining the provision of a single main cutting face and a single spiral flute with the comparably large rake angle, the drill bit according to the invention drill bit allows for minimizing heat production when drilling a hole into a bone.

Preferably, the rake angle is smaller than 40° or smaller than 35°. By dimensioning the rake angle in a range of 25° to 40° or to 35° it can be achieved that the drill bit's cross sectional wedge forming the cutting face is sufficiently firm and still an appropriate clearance between the drill bit and the bone can be provided during drilling. In particular, in a cross sectional view the wedge can define a wedge angle and the clearance a clearance angle. Thereby, the sum of the rake angle, the wedge angle and the clearance angle amounts to 90°.

Preferably, the spiral flute defines a helix angle which is smaller than the rake angle. Thereby, the helix angle can be defined by a land of the spiral flute and the axis of the longitudinal body. The spiral flute can also have plural varying helix angles along the axis. Also the transition between rake and helix angle can be anywhere along the axis. Providing a comparably small helix angle allows for efficiently forwarding bone chips created by the drilling process out of the hole. In known drill bits the helix angle typically is identical to the rake angle, i.e. the cutting face uniformly passes over into the spiral flute. Also in the drill bit according to the invention the main cutting face preferably passes over into the spiral flute. However, in accordance with the invention the rake angle is comparably high which, if the helix angle was the same, leads to a comparably flat spiral flute. By reducing the helix angle and particularly to an extent to be smaller than the rake angle it can be achieved that the spiral flute is comparably steep such that the chips can be forwarded more directly and efficiently along the spiral flute.

Preferably, the distal end of the body has a front profile orthogonal to the axis of the body and the cutting edge extends across the front profile of the distal end of the body. Thereby, the cutting portion of the cutting edge can cover around half the distance or half its extension. The term "across the front profile" in this connection can relate to a course from one side of a peripheral end of the front profile to an opposite side of the peripheral end of the front profile. Thereby, the opposite sides do not have to be strictly opposite in the sense of being 180° offset from each other around the periphery of the front profile. However, the offset of the opposite sides should be at least 90° or at least 105°, for example about 135°. Such a cutting edge allows, when drilling, for efficiently cutting the bone over the essentially complete circumference of the hole or the essentially complete front profile.

Preferably, the distal end of the body has a point located on the axis of the body. The point defines a point angle which is important for centering properties of the drill bit particularly on oblique surfaces. In particular, the point preferably defines a point angle in a range of about 70° to about 140° and more particularly a point angle of about 90°. By having a point angle in such a range it can be comparably small such that the point can be comparably sharp which allows for providing the mentioned centering properties.

The cutting edge preferably is offset from the point of the body. Such an arrangement allows for efficiently providing a continuous cutting edge and a point in parallel. Thereby, the small point angle makes it possible to minimize the offset wherein the functioning of the point for centering the drill bit can still be assured.

Thereby, a conical chisel face preferably is formed between the point of the body and the cutting edge. The conus of the chisel face can be comparably steep since the rake angle is comparably high. Thus the point can be comparably sharp which allows for efficiently providing its function within drilling.

Preferably, the body comprises a shaft extending from the proximal end along the axis. By embodying the drill bit with a proximal shaft a portion to be efficiently connected to a drill device can be provided. Thereby, the shaft can be suitably shaped in order to be connected to the drill. For example, the shaft can be cylindrical or irregularly profiled.

Thereby, the body preferably comprises a transition portion between the spiral flute and the shaft in which the spiral flute continuously passes over into the shaft. "Continuously passing over" in this context can mean a smooth transition which allows for reducing the risk of fracture of the drill bit. Providing the drill bit with the transition portion allows for continuously and efficiently forwarding and removing bone chips generated by the drilling process.

Preferably, the spiral flute has a distal end adjacent to the main cutting face and a proximal shallow end. The shallow end can be at a side of the spiral flute opposite to the main cutting face. Such a shallow end of the spiral flute allows for preventing the chips from breaking.

BRIEF DESCRIPTION OF THE DRAWINGS

The drill bit according to the invention is described in more detail herein below by way of an exemplary embodiment and with reference to the attached drawings, in which.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
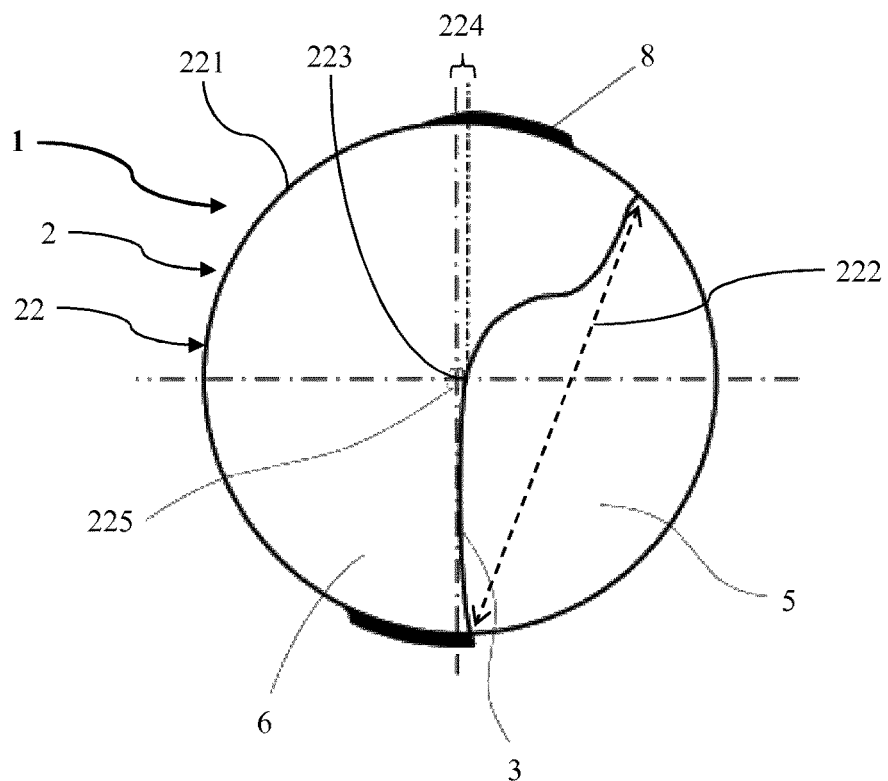
FIG. 1 shows a schematic front view of an embodiment of the drill bit according to the invention.

FIG. 1 shows a view on a distal end 22 of a body 2 of a drill bit 1 according to the invention. Thereby, a front profile 221 of the distal end 22 is visible wherein the front profile 221 extends orthogonally to an axis (not visible in FIG. 1) of the body 2. The drill bit 1 has a diameter which is constant over its whole length. For example, the diameter can be in a range from about 1.5 mm to about 4 mm or from about 2 mm to about 3 mm or it can be about 2.5 mm.

The drill bit 1 has a curved main cutting edge 3 or cutting lip which extends across the front profile 221 of the distal end 22 of the body 2 and which can be a sharp edge or a rounded edge. In particular, the main cutting edge 3 runs from one side of a periphery of the front profile 221 to an opposite side of the periphery of the front profile 221. Thereby, the main cutting edge 3 crosses the periphery of the front profile 221 at two different locations such that a peripheral cutting edge offset 222 of about 135° is defined.

Centrally or at the end of the axis (not visible in FIG. 1) the distal end 22 of the body 2 has a point 223. The main cutting edge 3 passes besides the point 223 across the front profile 221 such that a point offset 224 is defined as the closest distance between the point 224 and the main cutting edge 3. The point offset 224 is comparably small. For example, for a drill bit 1 with a diameter of about 2.5 mm it is in a range from about 0.03 mm to about 0.1 mm or about 0.04 to about 0.08 or it can be 0.05 mm. The range might vary for other diameters.

Between the point 223 of the body 2 and the cutting edge 3 a conical chisel face 225 is formed. The conus of the chisel face 225 is comparably steep such that the point 223 is comparably sharp. The drill bit 1 further comprises a flank portion 6 and one single spiral flute 5 or helix portion which enables evacuation of cut bone or chips. The design of the drill bit 1 allows minimizing a diameter of the chisel face 225 and comprises of a minimal asymmetry. Radially from two opposite sides of the flank portion 6 two corresponding margins 8 extend. The margins 8 can have a thickness in a range from about 0.1 mm to 0.5 mm. The margins 8 reduce the contact surface of outer drill bit diameter and a drilled hole. The drill bit 1 can also have less or more than two margins.

Figure 2:
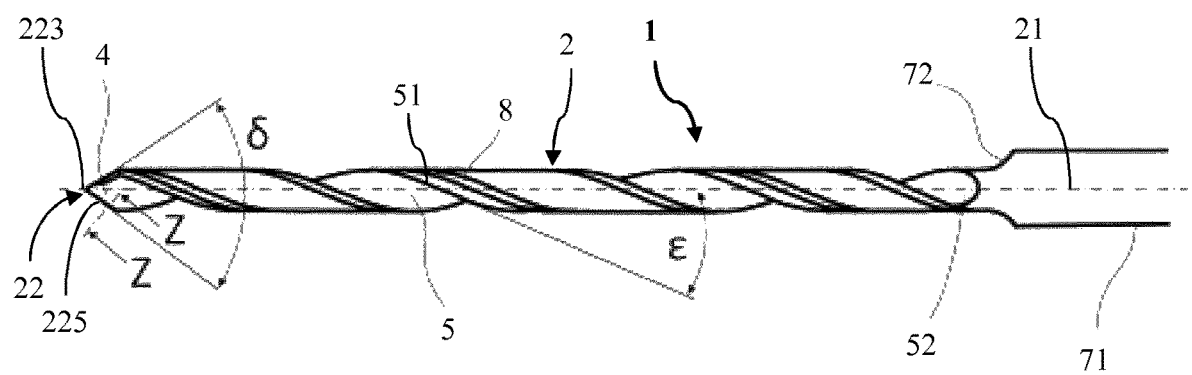
FIG. 2 shows a schematic side view of the drill bit of FIG. 1.

As can be seen in FIG. 2, the point 223 defines a point angle δ which is important for centering the drill bit 1 particularly on oblique surfaces. The axis 21 of the body 2 extends longitudinally along and centrally through the body 2. Between a land 51 of the spiral flute 5, which lies at the outer diameter of the drill bit 1, and the axis 21 of the body 2 a helix angle ε is defined. The helix angle ε is in a range from about 15° to about 35° which is comparably small. The helix angle ε defines how the spiral flute 5 winds around the axis 21 of the drill bit 1. It influences chip evacuation.

Starting at the main cutting edge 3 the drill bit 1 comprises a main cutting face 4 which passes over into the spiral flute 5. The distance of the cutting face 4 passing over into the spiral flute 5 can be in a range from about 1 mm to about 5 mm.

Towards a proximal end the body 2 of the drill bit 1 has shaft 71. Between the shaft 71 and a proximal helix end 52 of the spiral flute 5 a transition portion 72 is formed. In the transition portion 72 the spiral flute 5 smoothly passes over into the shaft 71. The transition portion 72 is designed with a radius to reduce vibration and fracture risk. The helix end 52 is designed with a smoothly transitioned shallow ending. The shaft 71 is dimensioned to fit a connection means of a drill. More particularly, it has a desirable length, diameter and design to allow coupling to a desired manual or electronic device, i.e. the drill device. This device can be set to any desirable parameter such as rotational speed, feed rate and the like.

Figure 3:
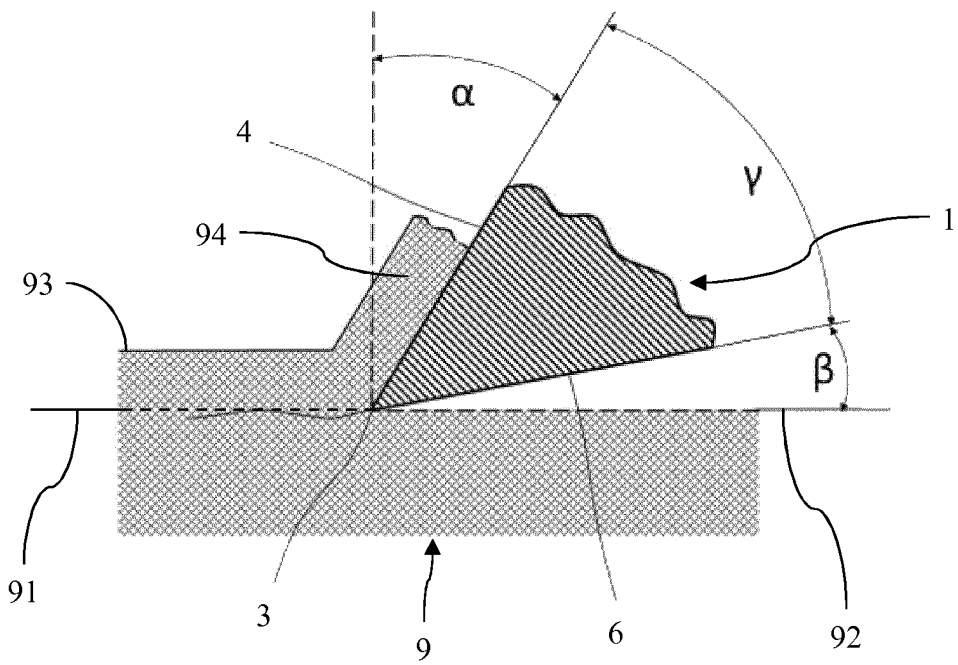
FIG. 3 shows a schematic cross sectional view of the drill bit of FIG. 1 along the line Z-Z of FIG. 2 in operation.

In FIG. 3 the drill bit 1 is schematically shown while being applied to a bone 9. The bone 9 has an original or old surface 93 which is the surface where the drill bit 1 has not acted on and a new surface 92 which is the surface where the drill bit 1 already did act on. In one plane with the new surface 92 lies an intended new surface 91 which is the surface to be generated by the drill bit 1 when being further applied. The main cutting face 4 upwardly from the main cutting edge 3 cuts the bone 9. Thereby, chips 94 are created of the bone 9 which are forwarded through the spiral flute 5.

The drill bit 1 has a rake angle α which is defined between the intended new surface 91 of the bone 9 and the main cutting face 4 less 90°. Or in other words, the rake angle is defined between a plane normal to the intended new surface 91 of the bone 9 and the main cutting face 4. The rake angle α is in a range of about 25° to about 35° which is comparably large. By dimensioning the rake angle α in such a range it can be achieved that the drill bit 1 cross sectional wedge forming the cutting face 4 is sufficiently firm and still an appropriate clearance between the drill bit 1 and the bone 9 is provided. In particular, in the cross sectional view of FIG. 3 the wedge can define a wedge angle γ. Furthermore, the clearance is formed by the flank portion 6 being angled with a clearance angle β. The clearance angle β avoids scratching of the material with elevated feed rate. The sum of the rake angle α, the wedge angle γ and the clearance angle β amounts to 90°. The clearance angle β is in range from about 15° to about 25°. Since the rake angle α is comparably high the point angle δ is comparably small such that the point 223 is comparably sharp.

In the following, an exemplary investigation is described in which a standard surgical drill bit was compared to custom drill bit as a further embodiment of a drill bit according to the invention. Both drill bits had a diameter of 2.5 mm. The custom drill bit was designed in accordance with the invention to generate less heat than the standard drill bit manufactured by Synthes, Johnson & Johnson, USA. A new experimental setup was developed to measure drilling forces and torques as well as the two dimensional (2D) temperature field at any depth at a distance of 0.5 mm to drilled hole using a high resolution thermal camera. The rotational speed was set to 1'000 rounds per minute (RPM) and the feed rate to 0.5 mm/s. The drilling depth was 25 mm and external irrigation rate was set to 30 ml/min. The drilled material was freshly frozen cortical bone from a 4 year old cow. Continuous intervals of 0.5 mm were drilled with an extraction of the drill bit in-between the intervals to allow intermittent cooling of the bone. The experiments were repeated 8 times and maximal elevation of temperature, force and torque of each interval was extracted over the whole drilling depth.

Figure 4:
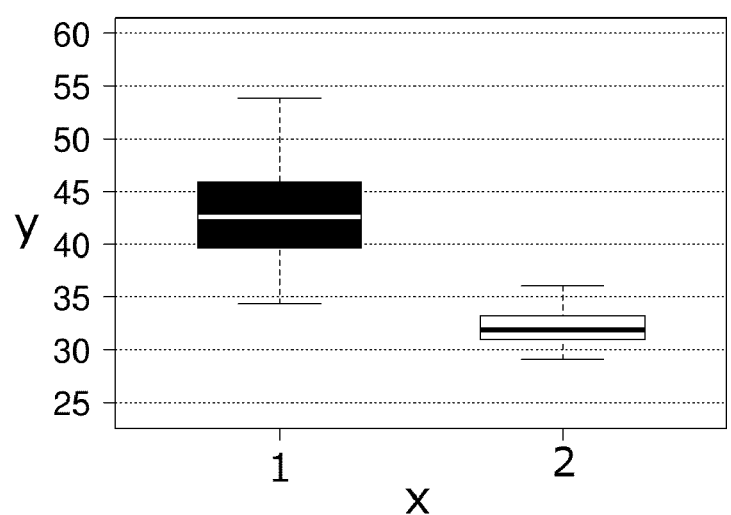
FIG. 4 shows temperature results of a test comparison between a standard drill bit and a custom drill bit as a further embodiment of the drill bit according to the invention.

FIG. 4 shows the maximal temperature elevation (y=Temperature [° C.]) for the standard drill bit (x=1) and the custom drill bit (x=2). Experiments were conducted at room temperature (24° C.) and temperature elevations were extracted for each interval over the whole drilling depth. The maximal temperature elevation of the custom drill bit is significantly lower (>10° C.) compared to the standard drill bit. This is important, because it limits the overall temperature rise to 34° C. (ΔT≈10° C. from room temperature). This can be converted to body temperature 37° C.+10° C.=47° C. which is the threshold of tissue damage. Therefore it is possible to drill with the custom drill bit without damaging the surrounding bone or other vulnerable structures such as nerves and the like. This is not possible with the standard drill bit.

Figure 5:
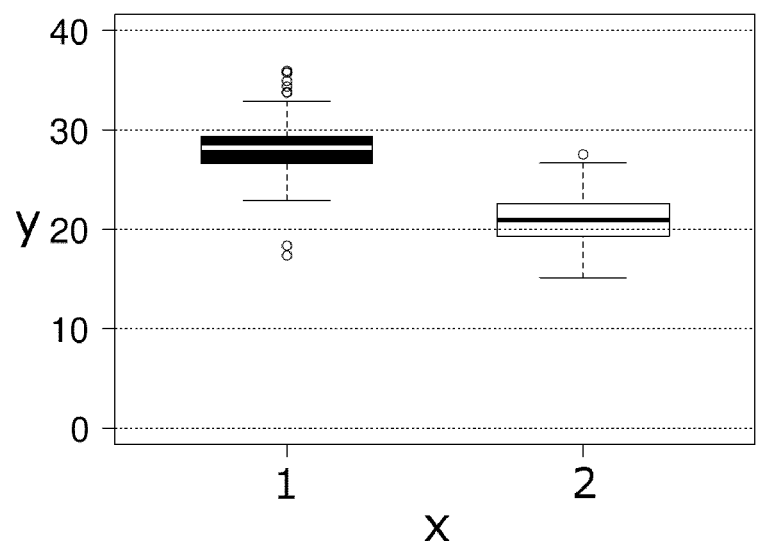
FIG. 5 shows thrust force results of the test comparison of FIG. 4.

In FIG. 5 the maximal axial thrust force (y=Force [N]) of the standard (x=1) and the custom drill bit (x=2) is shown. It can be seen that the force elevation of the custom drill bit is below the thrust forces of the standard drill bit.

Figure 6:
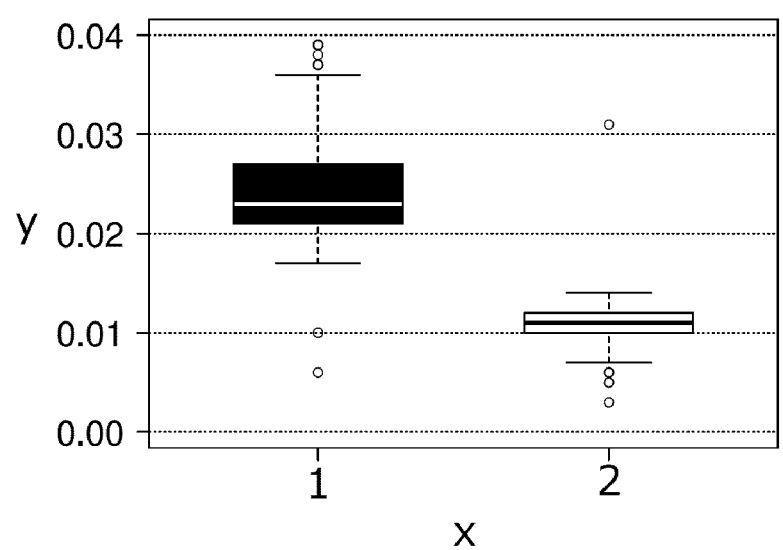
FIG. 6 shows torque results of the test comparison of FIG. 4.

FIG. 6 shows the maximal torque (y=Torque [Nm]) of the standard (x=1) and the custom drill bit (x=2). The torque of the custom drill bit is around half the value of the standard drill bit. Therefore, the custom drill bit is able to cut the material much more efficiently than the standard drill bit which explains the significantly lower temperature elevation.

This description and the accompanying drawings that illustrate aspects and embodiments of the present invention should not be taken as limiting-the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled or the like, or they may be indirectly coupled via one or more intermediate components. Any reference signs in the claims should not be construed as limiting the scope.

The invention claimed is:

1. A drill bit for creating a tubular hole in a bone, comprising:
   a longitudinal body extending along an axis and having a proximal end and a distal end, the distal end of the body comprising a conical chisel face formed between a point and a main cutting edge at the distal end of the body, the main cutting edge being offset from the point;
   a main cutting face extending from the main cutting edge and defining a rake angle; and
   a spiral flute formed around the body and extending from the main cutting face along the axis of the body;
   wherein the main cutting edge is the only single main cutting edge of the drill bit,
   wherein the spiral flute is the only single spiral flute of the drill bit,
   wherein the rake angle is at least 25°,
   wherein the distal end of the body has a front profile orthogonal to the axis of the body and the main cutting edge extends across the front profile of the distal end of the body,
   wherein the main cutting edge extends across the front profile of the distal end of the body at two different locations of a periphery of the front profile, and
   wherein the two different locations are positioned from each other within a range of 90° to 180° offset from each other.

2. The drill bit according to claim 1, wherein the rake angle is smaller than 40°.

3. The drill bit according to claim 1, wherein the drill bit is configured to generate an intended new surface of bone, wherein the rake angle is defined between the intended new surface of the bone and the main cutting face of the drill bit and, wherein the rake angle is less than 90°.

4. The drill bit according to claim 3, wherein the intended new surface of the bone is an inner surface of the tubular hole.

5. The drill bit according to claim 1, wherein the spiral flute defines a helix angle which is smaller than the rake angle.

6. The drill bit according to claim 5, wherein the helix angle is defined between a land of the spiral flute and the axis of the longitudinal body.

7. The drill bit according to claim 1, wherein the main cutting face passes over into the spiral flute.

8. The drill bit according to claim 1, wherein the point is located on the axis of the body.

9. The drill bit according to claim 8, wherein the point defines a point angle in a range of about 70° to about 140°.

10. The drill bit according to claim 8, wherein the main cutting edge extends from the point within a range of 0.03 mm to 0.1 mm.

11. The drill bit according to claim 1, wherein the body comprises a shaft extending from the proximal end along the axis.

12. The drill bit according to claim 11, wherein the body comprises a transition portion between the spiral flute and the shaft in which the spiral flute continuously passes over into the shaft.

13. The drill bit according to claim 1, wherein the spiral flute has a distal end adjacent to the main cutting face, and wherein the spiral flute comprises a shallow proximal end.

\* \* \* \* \*